Nov. 20, 1962 F. W. ANDERSON Plant Pat. 2,192

APRICOT TREE

Filed Jan. 19, 1962

WITNESS

Addison I. Avery

INVENTOR

Frederic W. Anderson

Webster & Webster

ATTYS.

United States Patent Office

Plant Pat. 2,192
Patented Nov. 20, 1962

2,192
APRICOT TREE

Frederic W. Anderson, Merced, Calif., assignor to Kim Bros., Reedley, Calif., a copartnership Filed Jan. 19, 1962, Ser. No. 167,456
1 Claim. (Cl. 47—62)

This invention relates to a new and distinct variety of apricot tree, particularly characterized, as to novelty, by the early ripening period of the fruit; the latter being in harvest in the last week of May and the first week of June.

As compared to well known existing commercial varieties of apricots, the ripening period of the fruit of the present variety is—on the average—several days before the Newcastle and Derby; more than a week before the Perfection; approximately two and a half weeks before the Blenheim or Royal; and more than three weeks before the Tilton. All of the foregoing varieties are unpatented.

The present variety is further characterized by a tree that is very large and productive, and by fruit having flesh that is quite firm at shipping stage and of good quality when eating ripe; the fruit being larger than the Royal; smaller than the Perfection; and about the size of the Tilton.

The herein claimed variety of apricot tree was originated by me, in my experimental orchard located near Merced, California, as a second generation seedling ($P_2$) of the Perfection. More particularly, a large number of seeds, from open pollinated flowers of the Perfection, were planted and selections thereafter made from the earliest ripening of the resultant first generation ($P_1$) seedlings. Seeds from open pollinated flowers of such selected first generation seedlings produced a number of early ripening second generation ($P_2$) seedlings and from which—after careful and continued observation—I selected the instant variety as having the most desirable characteristics.

Subsequent to the origination and selection of the variety, as above, I asexually reproduced it, in my experimental orchard located as aforesaid, by scions grafted on older apricot seedlings; such reproductions having run true in all respects.

Figure 1:
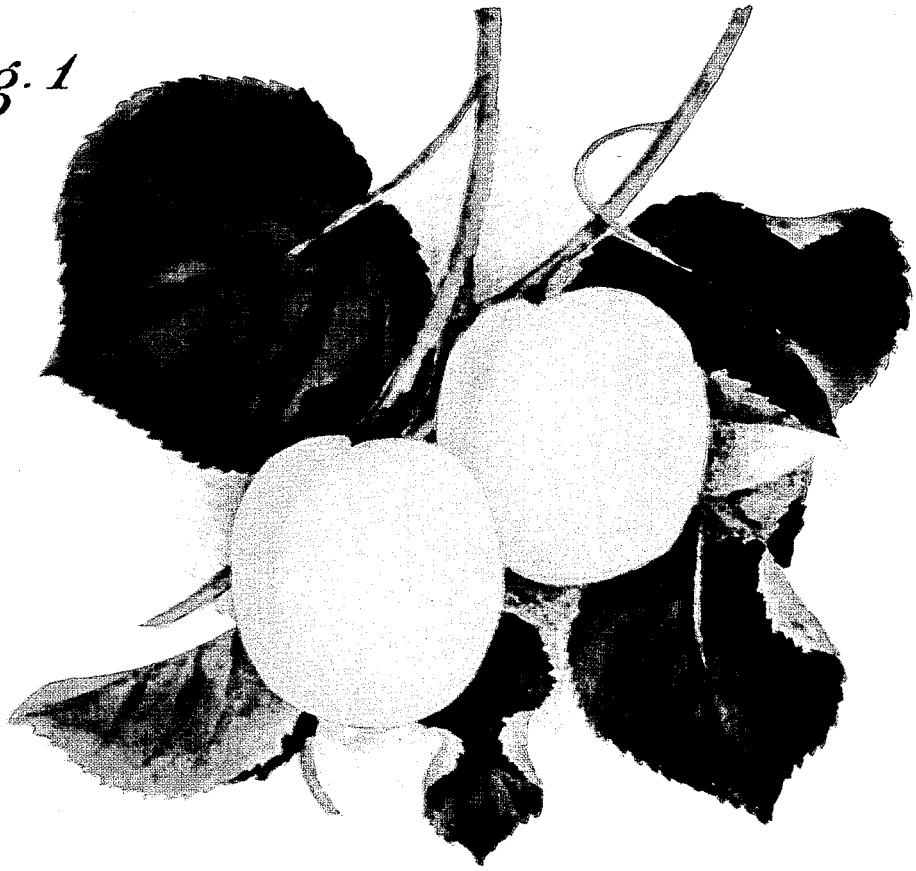
FIG. 1 is an elevation showing two of the fruits, together with twigs and leaves.
Figure 2:
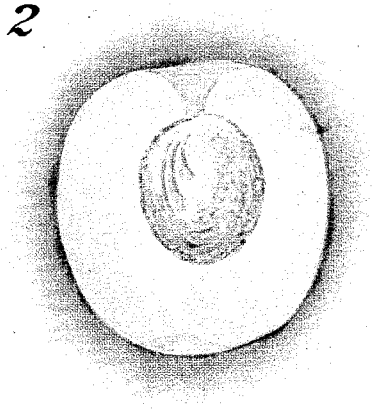
FIG. 2 is a sectional elevation of one of the fruits with the stone remaining in place.
Figure 3:
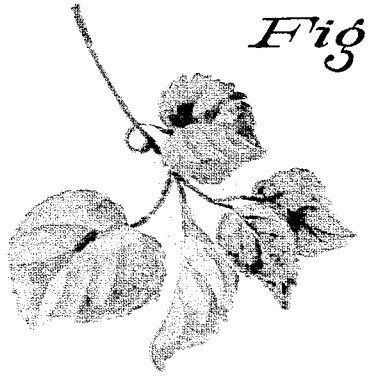
FIG. 3 is a view showing small terminal leaves.

Referring now specifically to this new and distinct variety of apricot tree, the following is a detailed pomological description thereof in outline; all major color plate identifications being by reference to Maerz and Paul Dictionary of Color, except where common terms of color definition are employed:

Tree:
- *Size.*—Large.
- *Vigor.*—Vigorous.
- *Form.*—Vase formed; spreading.
- *Density.*—Open.
- *Production.*—Productive.
- *Bearing.*—Regular bearer.

Trunk: Texture—medium.

Branches:
- *Size.*—Medium
- *Texture.*—Medium.
- *Lenticels.*—Numerous; medium size.

Leaves:
- *Size.* — Large. Average length — 2⅝". Average width—2⅜".

- *Form.*—Cordate.
- *Thickness.*—Medium.
- *Texture.*—Smooth.
- *Margin.*—Finely serrate.
- *Petiole.*—Long; medium thickness.
- *Glands.*—Average number and position—three or four, usually on petiole. Alternate; small; red.
- *Color.*—Top side—medium green (20–L–7). Under side—lighter green (20–I–6). Small terminal leaves—olive yellow (14–L–2), shading to a bronze (14–L–10).

Flower buds:
- *Size.*—Medium.
- *Length.*—Medium.
- *Form.*—Conic.

Flowers:
- *Blooming period.*—Early, about four or five days before the Royal.
- *Size.*—Large.
- *Color.*—White.
- *Fertility.*—Self-fertile.

Fruit:
- *Maturity when described.*—Eating ripe—May 30, 1961.
- *Date of first picking.*—May 27, 1960.
- *Date of last picking.*—June 5, 1960.
- *Size.*—Uniform to variable; medium. Average diameter axially—2⅛". Average transversely in suture plane—2⅛". Six to eleven to the pound.
- *Form.*—Uniform; symmetrical; globose.
- *Suture.*—Distinct; extends from base to apex.
- *Ventral surface.*—Rounded.
- *Cavity.*—Rounded, with suture showing on one side. Average depth—7/16". Average breadth—9/16". Markings—usually some red surface color (1–I–10).
- *Base.*—Rounded.
- *Apex.*—Depressed.
- *Pistil point.*—Lacking.

Skin:
- *Thickness.*—Medium.
- *Texture.*—Medium.
- *Tendency to crack.*—None noted.
- *Down.*—Scant; short.
- *Color.*—Apricot yellow (9–K–7, shading to 9–I–9).

Flesh:
- *Texture.*—Medium; meaty.
- *Ripens.*—Even.
- *Flavor.*—Subacid; delicate.
- *Aroma.*—Distinct.
- *Eating quality.*—Good.
- *Color.*—Yellow (9–K–7 to 9–K–9), shading lighter (9–I–3) particularly near stone. Surface of pit cavity—yellow.

Stone:
- *Type.*—Free.
- *Size.*—Medium. Average length—1". Average breadth—⅞". Average thickness—⅜".
- *Form.*—Oblong.
- *Apex.*—Rounded.
- *Sides.*—Equal.
- *Tendency to split.*—None noted.
- *Color.*—Buff (9–F–5), shading to beige (5–A–10), with some brown (8–L–11).

Use: Market.

Keeping quality: Medium.

Shipping quality: Good.

The tree and its fruit herein described may vary in slight detail due to climatic and soil conditions under which this variety may be grown; the present description being of the variety as grown in the Central Valley of California.

The following is claimed:

A new and distinct variety of apricot tree, as illustrated and described, which is large, productive, and bears fruit that is firm at shipping stage and of good quality when eating ripe; the fruit being larger than the Royal, smaller than the Perfection, and approximately the size of the Tilton; particularly characterized, as to novelty, by an early ripening period of the fruit and which is normally in harvest, in the Central Valley of California, during the last week of May and the first part of June.

No references cited.